United States Patent

Davis et al.

[11] Patent Number: 5,265,482
[45] Date of Patent: Nov. 30, 1993

[54] METHOD OF SAMPLING A CONTAINER

[75] Inventors: James E. Davis, Wilmington; Edward A. Nuzzaci, Newark, both of Del.

[73] Assignee: E. I. Du Pont de Nemours and Company, Wilmington, Del.

[21] Appl. No.: 703,826

[22] Filed: May 21, 1991

[51] Int. Cl.⁵ .............................................. G01N 1/14
[52] U.S. Cl. ............................................. 73/863.01
[58] Field of Search ........... 73/863.01, 804.23–864.25, 73/290 R, 304 C; 422/100; 324/672, 674, 676, 678, 679, 681, 683, 690

[56] References Cited

U.S. PATENT DOCUMENTS

| | | | |
|---|---|---|---|
| 3,391,547 | 7/1968 | Kingston | 62/218 |
| 3,635,094 | 1/1972 | Oberli | 73/423 |
| 3,852,194 | 12/1974 | Zine, Jr. | 210/83 |
| 3,939,360 | 2/1976 | Jackson | 307/118 |
| 4,002,996 | 1/1977 | Klebanoff et al. | 331/65 |
| 4,099,167 | 7/1978 | Pomerantz | 340/620 |
| 4,371,790 | 2/1983 | Manning et al. | 307/118 |
| 4,818,492 | 4/1989 | Shimizu | 422/100 |
| 4,873,875 | 10/1989 | Cork | 73/863.01 |
| 5,017,909 | 5/1991 | Goekler | 73/304 C |

FOREIGN PATENT DOCUMENTS

| | | | |
|---|---|---|---|
| 2066961 | 7/1981 | United Kingdom | 73/304 C |
| 2074325 | 10/1981 | United Kingdom | 73/304 C |

Primary Examiner—Robert Raevis

[57] ABSTRACT

A container is scanned bottom-to-top and top-to-bottom with a capacitive sensor to detect liquid interfaces therein. The interfaces are coded, have their height stored and have their codes compared to determine the internal consistency. If consistent, the code and height information is used to sample a desired layer.

6 Claims, 6 Drawing Sheets

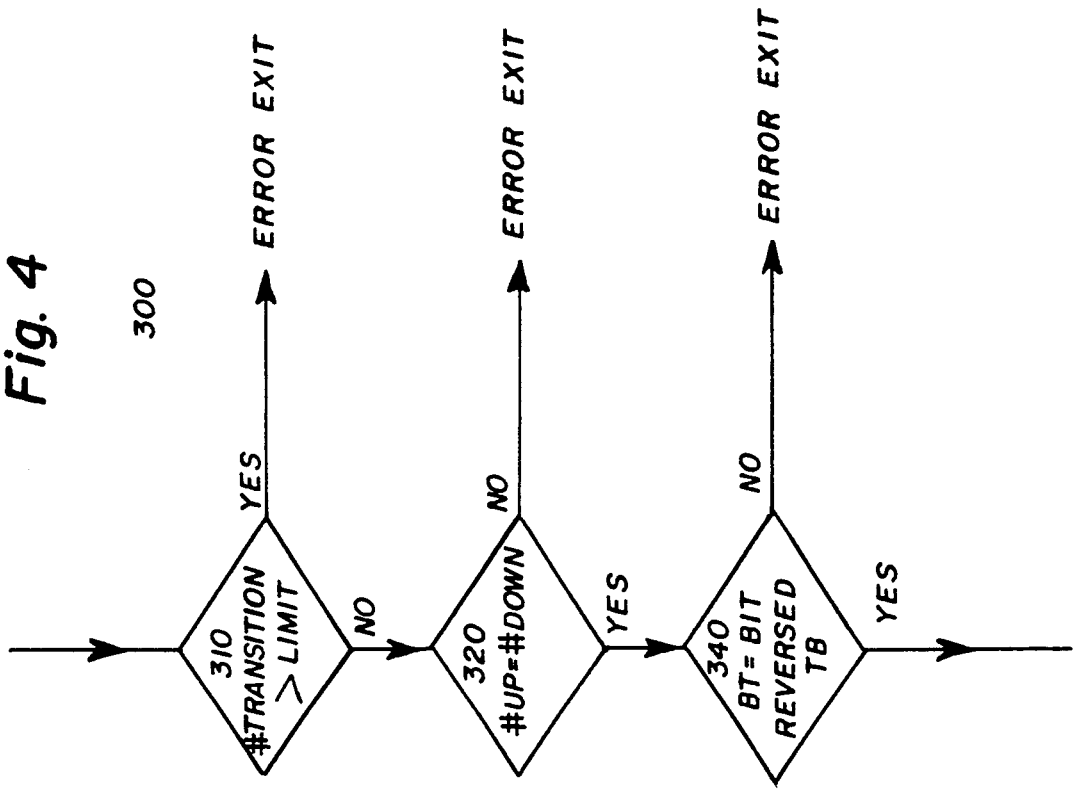

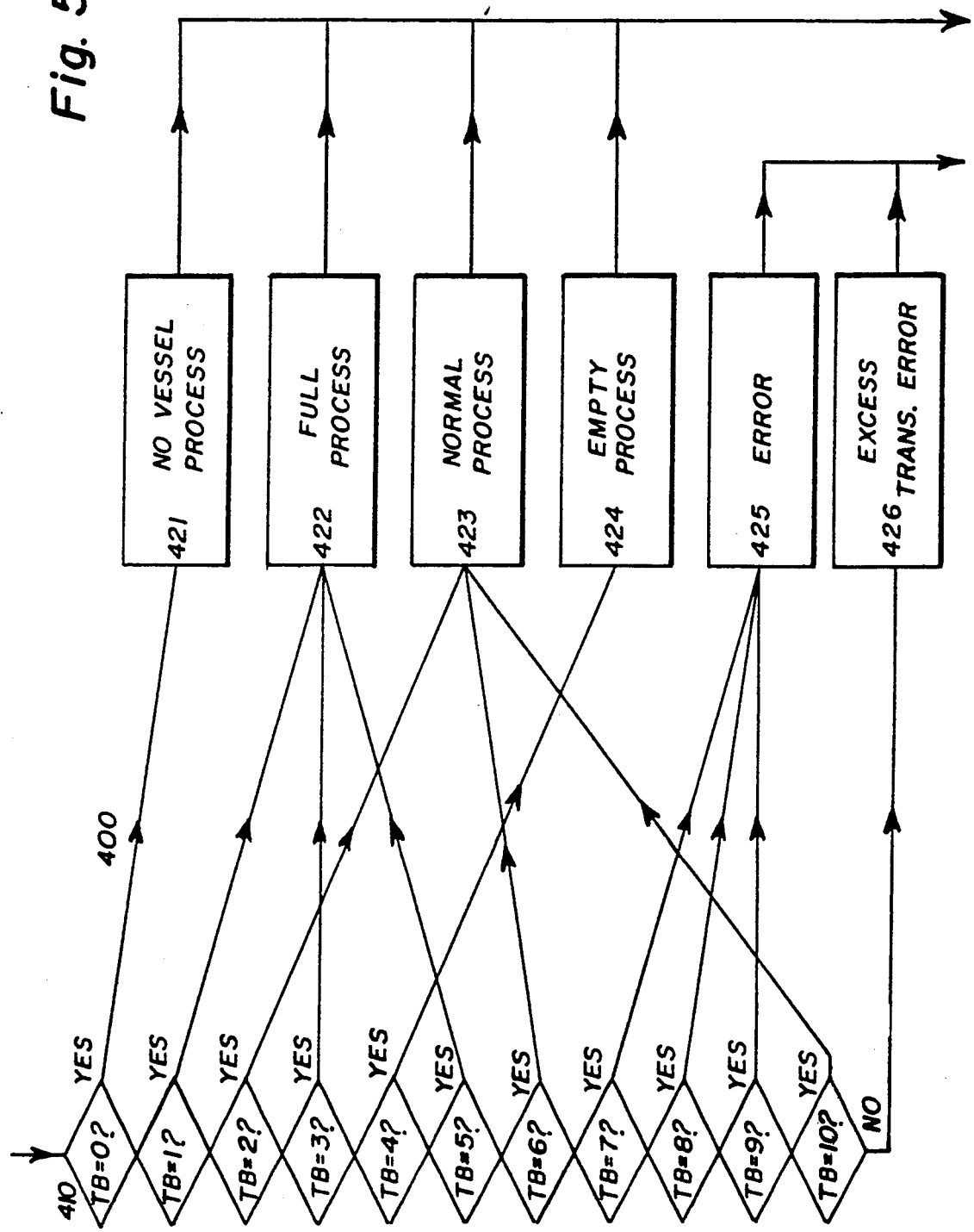

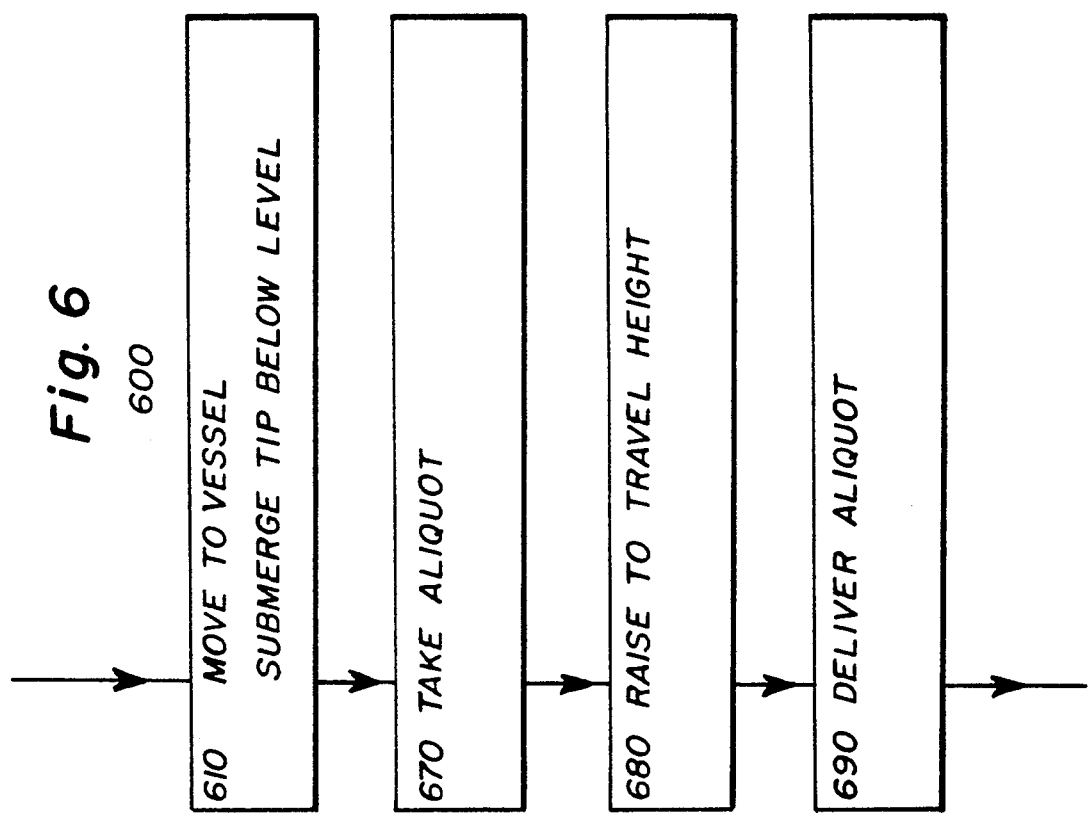

METHOD OF SAMPLING A CONTAINER

CROSS-REFERENCE TO RELATED APPLICATIONS

This application contains subject matter described in a copending application for Capacitive Liquid Interface Sensor, Ser. No. 07/466,938, filed Jan. 18, 1990.

BACKGROUND OF THE INVENTION

This invention relates to capacitive liquid level sensors used to control the sampling of liquids from a container. It also relates to capacitive sensors capable of sensing the interface between different layers, including air. Such liquid level sensors find use in many instruments wherein a robotic probe is used to withdraw liquid from a container, containing a sample to be analyzed or a reagent, in a controlled manner.

In such robotic systems, it is desirable to have knowledge of the level of the liquid at the interface between liquids in the container such that the probe used to withdraw the liquid can be controlled (1) to withdraw a particular layer of liquid in the container or (2) to minimize contact with an undesired portion or layer of the liquids in the container. In such systems, one is dealing with generally separable fluids such as occurs in the collection of blood. In a typical blood system producing packed red blood cells, the red blood cells will be in the lower portion of the container. Immediately above the packed cells is a commercial separation gel as described in U.S. Pat. No. 3,852,194 to Zine. Above the separation gel is the serum or plasma and finally air is on the top. Contamination of the sampling probe by the separation gel is very undesirable. Often it is relatively difficult to remove the gel from the probe and the gel can in fact cause clogging of the probe and missampling to occur. Therefore it is highly desirable to provide some system of locating the gel-serum interface so that the serum only can be withdrawn and the probe prevented from contacting the gel.

To accomplish this objective, it is necessary to be able to sense the level of the liquid interfaces on a real time basis. Various level sensors have been developed for this purpose. Among those are the so-called capacitive level sensors. These are based on the fact that any conductor (say a sensing probe) exhibits a finite electrical capacitance. This capacitance, when approaching a liquid having a higher dielectric constant, will increase. When the sensing probe is in close proximity to a liquid, the higher dielectric constant and greater surface area results in an increased capacitance of the probe. These capacitance changes caused by the liquid can be rather small so that sensitive detection devices are required.

Devices known in the prior art that are suitable for detecting small changes in capacitance include bridges, RC or LC oscillators and frequency meter counters (including heterodyning), phase locked loops, zero crossing periodometers, amplitude changes to an RC or LC filter, and phase shift changes through an RC or LC circuit.

Among the prior art capacitive liquid level sensors is Kingston U.S. Pat. No. 3,391,547 which discloses a capacitive liquid level probe for a liquid tank. He utilizes a capacitor probe, disposed in the liquid, as one leg of a bridge circuit. An unbalance in the circuit, as a result of change in capacitance of the probe, is detected by a phase sensitive detector which is referenced by the fixed frequency excitation oscillator through a variable phase shifter. The variable phase shifter allows for offset adjustment.

In similar manner, Oberli U.S. Pat. No. 3,635,094, discloses a capacitive level sense means for an automatic transfer pipette. The sample probe is utilized as the first element and a metal stand around the sample vessel is the second element which forms a capacitor in one leg of a bridge circuit. The remaining legs of the bridge consist of a variable capacitor leg and two resistor legs. The variable capacitor leg may be adjusted such that its capacitance matches that of the probe contacting the liquid. The bridge circuit is excited by a fixed frequency oscillator and a differential amplifier is utilized to determine when the bridge is balanced indicating that the probe has contacted the liquid.

Finally, Shimizu U.S. Pat. No. 4,818,492 discloses a capacitive liquid level sensor for an automatic clinical analyzer. The output is filtered and compared against a reference value to provide a signal indicating the presence of liquid at the probe.

None of these sensors are directed to sensing the liquid interfaces in any useful fashion as the probe must disturb such interfaces as it journeys down through the tube or container. To solve this problem, various systems have been devices which seek to determine liquid level from the exterior of a container. Typical of these systems are those described in U.S. Pat. No. 4,099,167 and U.S. Pat. No. 4,002,996. In both of these systems electrodes are disposed on the exterior of the container and changes in the dielectric provided by the contained liquid as compared to air is sensed by causing a variation in a capacitance sensitive detector. Another system such that described in U.S. Pat. No. 4,371,790 uses the electrical conductance of a liquid to determine the level of the liquid contained in a container.

Finally, U.S. Pat. No. 3,939,360 describes a similar system in which a tape is attached or fixed to the outside of a container whose liquid level is to be sensed. Unfortunately such system is unable to seek the level of liquid-/air interface but must allow the interface to pass by its location before such is detected.

The problem with these latter interface sensors is that while they are able to sense the interface between liquid levels, they are not able to ascertain whether there is sufficient fluid in a particular layer to sample, whether there was some error in creating the liquid levels which resulted in the absence of a particular layer, or whether the liquid container is normal. These additional factors must be ascertained if adequate sampling is to be accomplished.

SUMMARY OF THE INVENTION

Many of these problems inherent in the prior art sensors inability to reliably sense the location of liquid interfaces and condition of the liquids in the container, and whether there is sufficient liquid to sample, are reduced with the use of the subject invention. This invention provides a means to reliably determine information relative to layers of liquid in a container, their height (volume), and ability to withdraw sample from the layers. This information can be used to control the movement of the probe and prevent it from entering undesired regions and/or directed to the precise location desired between layers of liquid.

In accordance with the preferred embodiment of this invention, a capacitive sensor is used for controlling the sampling of liquids from a container by a probe, the liquids being held in a container having a generally vertical axis, comprising the steps of: scanning along the container axis in a first sense to detect increasing or decreasing capacitance transitions therein, assigning each such transitions a different binary bit which are according to the increasing or decreasing nature of the transition, thereby forming a first binary code, recording the height along the axis corresponding to each said transition, actuating the probe to sample the container only if the proper number of transitions for the liquids in the container have occurred, and controlling the depth at which the probe samples in accordance with the first binary code and the height.

When a sensor of this type is used with an element that mechanically scans a blood collection tube from the outer surface of the tube, as the element encounters the base of the tube (end opposite the stopper) the capacitance increases because of the proximity of the packed red cells which medium is of high dielectric and conductive. Next the element encounters a separation gel which medium has a low dielectric and is not conductive resulting a decrease in capacitance. For purposes of this invention, the gel is considered to be a liquid. The "gel" may be beads or other structures used for separating fluids of a different density.

Next the element encounters serum or plasma which medium is of high dielectric and conductive. Finally the element encounters a zone of air which medium is of low dielectric and not conductive. Thus the capacitance of the sensing element increases to some relatively high value through the red cell zone then abruptly decreases at the gel interface, then abruptly increases at the serum interface and finally abruptly decreases at the air interface. These abrupt changes are discriminated and used to create a binary code that is representative of the sequence of the transitions that can be used to control the sampling probe.

In a preferred embodiment of this invention the number of transitions is counted and compared to a predetermined number. If the number of transitions does not equal a predetermined number the probe may be disabled. Also the first binary code may be formed by shifting the code to the left one bit for each transition and adding one to the lowest order bit position if the transition is of increasing nature. The method may also include the additional step of scanning along the container axis in a second sense to detect the capacitance transitions therein, and assigning such transitions different binary bits according to the increasing or decreasing nature of the transitions, thereby forming a second binary code, and reconciling the first and second binary code. The codes may be reconciled by the steps of a) reversing the order of the second binary code, b) complementing the result of step a), and c) comparing the result of steps a) and b) for equality. Alternatively the codes may be reconciled by the steps of a) providing a lookup table that provides an equivalent first code for each of the sequential transitions which form the second code, and b) comparing the first and second codes for equality at each transition.

In this manner the condition of each container is immediately apparent. It is known based upon the sequence and state of the several transitions to be either full, normal, empty or an error condition exists indicating it's none of the above and the sampling should not take place. The system is extremely reliable if the double scan is used, i.e., scanning from the bottom to the top and thereafter from the top to the bottom and comparing the scanning results.

BRIEF DESCRIPTION OF THE DRAWINGS

A more complete understanding of the invention and its advantages may be understood in connection with the accompanying drawings in which:

FIG. 4 is a flow chart depicting the manner in which the CPU reconciles the scan data;

FIG. 5 is a decision chart depicting the manner in which the CPU recognizes the conditions of the sample.

FIG. 6 is a flow chart depicting the manner in which the CPU controls the aliquoting of sample fluid.

DESCRIPTION OF THE PREFERRED EMBODIMENT

Figure 1:
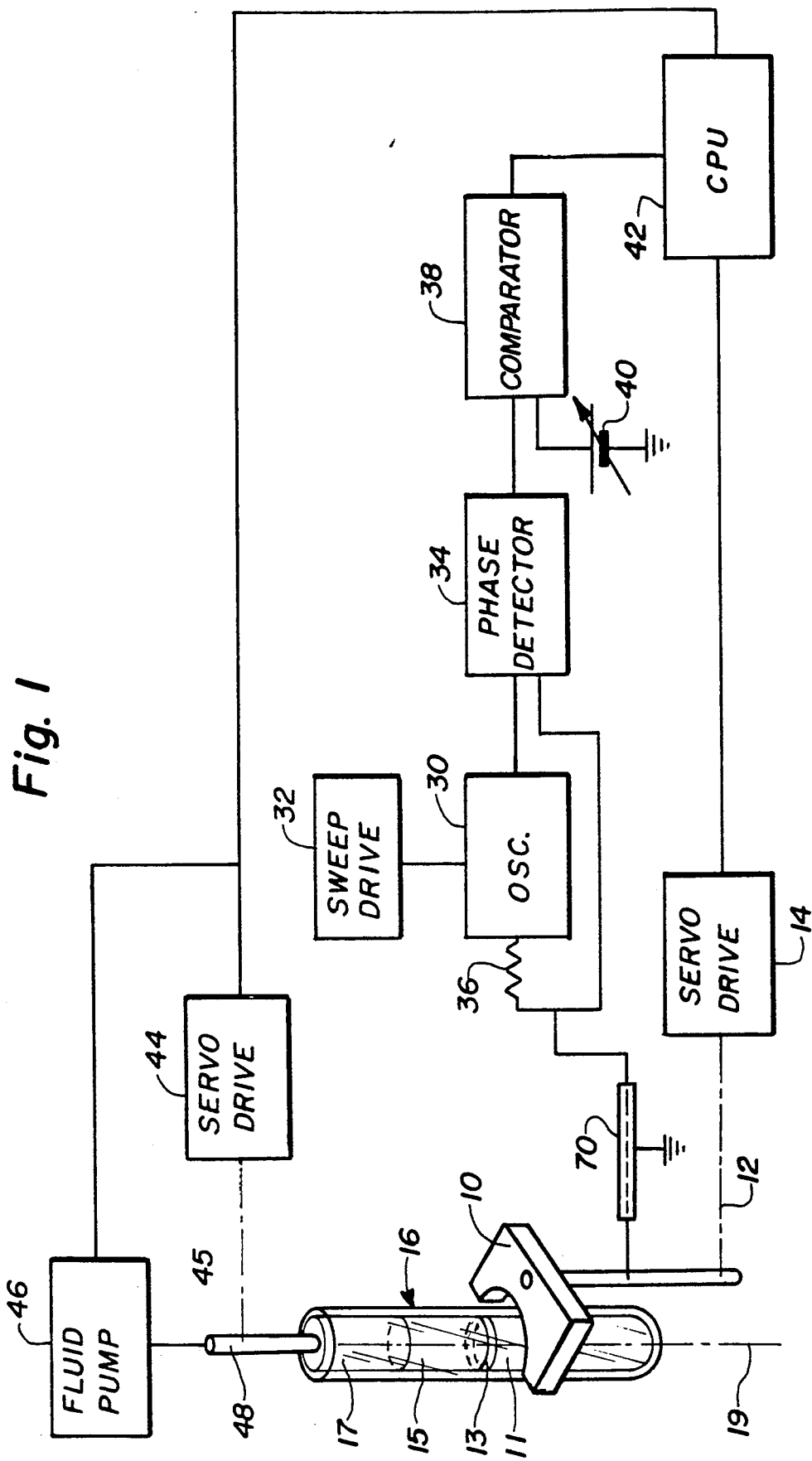
FIG. 1 is a block diagram of a liquid interface sensor constructed in accordance with this invention.

Reference is now made to the drawings in which FIG. 1 illustrates a position sensing element 10 driven by a robotic arm 12 which is controlled by a servo drive 14 of conventional design. The element 10, translated in the X, Y, and Z directions by the servo drive 14 of conventional design, is adapted to be positioned adjacent any one of plural sample, reagent or reaction containers 16 (only one of which is shown).

Each sample or reagent containers 16 has an axis 19 and will be described in connection with a typical use of this invention which is the use in connection with a blood collection tube. In such a blood collection tube, the container 16 could have packed red cells in the lower portion 11 separated by a gel 13; a serum 15 would be above the gel layer 13 and finally air 17 would be on the top. The sensing element 10 is adapted to traverse the exterior portion of the container 16 in a direction generally parallel to the axis 19, i.e., the Z direction. The element 10 is a flat metallic plate preferably of some relatively inert material such as stainless steel or platinum and is shaped to partially conform to the exterior curvature of the container 16. The element 10 is relatively thin; typically ⅛ of an inch. The packed red cells constitute a relatively high dielectric and conductance. On the other hand the separation gel 13 is a medium of low dielectric and is not conductive. The serum medium 15 has a high dielectric and conductance. The air zone however 17 is of low dielectric and low conductance.

This invention deals with a method of using these changes in capacitance caused by the different dielectrics, which represent the location of interfaces between the several layers of liquids in the container 16, to ascertain if the container should be sampled and if so to control the coupling. The changes in capacitance may be sensed by any suitable method or apparatus. A preferred apparatus, the one described by Davis, will now be described.

A pipettor or probe 48 for removing liquids from the container 16 is coupled through a flexible coupling such as a plastic tube to a fluid pump 46. The pipette is operated by a linkage 45 which in turn is positioned by a servo drive 44 which raises and lowers the pipette 48. The servo drive 44 and the fluid pump 46 are both actuated in turn by the CPU 42 using any known conventional system for this purpose. One such system is that known as the Dimension ™ Analyzer sold by E. I. du Pont de Nemours and Company, Wilmington, Del.

An oscillator 30 is coupled to an electrically conductive element 10 through a resistor 36 and coaxial cable 70 whose sheath is grounded. In turn, the oscillator 30, which may be a voltage controlled oscillator (VCO), may be connected to be swept in voltage by a sweep drive 32 which preferably provides a linear (e.g., triangular or sawtooth) waveform such that the oscillator is successively swept through a range of frequencies. Abrupt changes in the probe capacitance, which occur when the probe contacts a liquid, generate a spectrum of frequencies in the output of the detector. The sweep oscillator preferably sweeps the high frequency oscillator frequency at a repetition frequency above those frequency components generated by abrupt changes in probe capacitance. The oscillator 30, preferably is a voltage controlled oscillator, as noted, or similar oscillator whose frequency can be varied as result of an input signal.

The output of the oscillator is coupled to a phase detector 34 preferably capable of providing a D.C. output voltage. In this manner the phase detector is subjected to the shift in phase or amplitude caused by a change in the dielectric to which the element is subjected. There is a stray capacitance between the probe element and liquid in the container 16. When the element encounters a liquid of higher or lower dielectric constant, an interface is recognized and the output of the phase detector is a D.C. signal which varies in accordance with the changing capacitance sensed by the element.

A comparator 38 compares the signal from the phase detector 34 with a reference obtained by an adjustable voltage source 40. The output of the comparator is applied to a central processing unit (CPU) 42 which in turn is programmed to control the servo drive 14 in any conventional manner such as that described in U.S. Pat. No. 4,818,492. It controls the pipettor 38 to suck liquid from the container 16 at a height Z that was identified by the sensor. Thus the central processing unit 42 controls both the position of the pipettor 48 and whether the pipettor sucks up fluid from a container in accordance with the position sensed by element 10. Such central processing units are well known and will not be described further since they do not relate to the particular invention which is a liquid interface sensor.

In operation the element 10 as moved axially along the outer external surface of container 16 which by way of illustration may contain blood separated into red cells 11, gel 13, and serum 15. As the element 10 encounters the base of the tube 11 containing the packed red cells the capacitance increases because of the proximity to packed red cells which medium is of high dielectric and is conductive. Next the element 10 encounters the separation gel 13 which medium is of low dielectric and is not conductive. Next the element encounters the serum 15 which medium is of high dielectric and is not conductive. Finally the sensing element 10 encounters the zone of air 17 which medium is of low dielectric and is not conductive.

Correspondingly, the capacitance increases to some relatively high value through the red cell zone, abruptly decreases at the gel interface 13, then abruptly increases at the serum interface 13-16 and finally abruptly decreases at the air interface 15-17. These abrupt changes are discriminated and correlated to the mechanical position of the sensing probe 10 by the method set forth and described in flow charts of FIGS. 3-7.

The CPU is programmed to cause the sensing element of this invention to scan a vessel and to store for subsequent use the height and nature (increase or decrease in capacitance) of the transitions. Later, when the vessel previously scanned is to be accessed, the CPU commands the pipettor probe to be positioned over the vessel.

Generally the container is scanned from the bottom up so that the sensing element always begins in a known state (i.e. vs. air). The top may be inaccessible or cluttered with a stopper.

In ordinary circumstances for a blood collection container, the last capacitance transition is a decrease, corresponding to the serum to air interface. The previous transition will have been an increase in capacitance, corresponding to the gel to serum interface, or the bottom of the tube (i.e. absence of gel). In the former there will be an additional transition corresponding to the packed-cell to gel interface. In all events, the pipettor probe would be positioned with the tip approximately 1 mm under the surface of the serum, but if that would position it within 5 mm of the gel, then the sample procedure is not attempted because of its liability to clog and otherwise contaminate the sampling probe. The gel is distinguished from the bottom of the container by the known position of the bottom which is fixed by the design of the instrument. In the event of non-attempt to sample, the operator is expected to transfer the serum to another container which has no gel.

In some circumstances the last capacitance transition may be an increase. This may occur if the container is completely full such that the sensor element is unable because of mechanical constraints to scan to or past the top of the container. In this case, the serum to air interface is given a default value, however the gel to serum interface (if present) is still valuable information needed to prevent pipettor probe travel into the gel.

If a substantial amount of serum is to be taken, the pipettor probe is programmed to descend into the vessel at a rate to match the computed fall in height as the serum is withdrawn. Again, the maximum travel of the pipettor probe must be restricted to avoid contamination by gel.

When the sensor element scans the container, each capacitance transition causes three actions, 1) the position (height) of the sensor element is entered into a table, 2) the number of transitions is increased by one, and 3) the nature of the transition (increase or decrease in capacitance) is entered into a table.

The table of transitions is converted to or was formed as a binary word with (for example) the increases in capacitance stored as a bit with a value of one. The transition code is interpreted as a binary number. The number is used as an index into a table of cases. Thus, all possible codes are enumerated and each is categorized so that data processing appropriate to every possible condition is covered. For example, as applied to blood collection tubes or containers that may contain a commercial gelled separation aid that will be found between the packed blood cells and the serum or plasma, the possible conditions corresponding to the transition code is listed in Table 1.

TABLE 1

TRANSITION CODE WITH CORRESPONDING CONDITIONS

| VALUE | TRAN-SITION CODE | CONDITION | PROCESS # |
|---|---|---|---|
| 0 | 0 | No vessel or empty vessel or malfunction | 1 NO-VESSEL |
| 1 | 1 | Excess fluid or air interface not found | 2 FULL |
| 2 | 10 | Air above fluid (possible cells below fluid but interface not detected above above gel, i.e., no serum left-operator error) [note: gel thickness is limited and is known] | 3 NORMAL |
| 3 | 11 | Excess fluid above gel/cells or malfunction | 2 FULL |
| 4 | 100 | Air above gel above cells, i.e., no serum left | 4 EMPTY |
| 5 | 101 | Excess fluid above gel above cells/malfunction | 2 FULL |
| 6 | 110 | Air above serum above gel | 3 NORMAL |
| 7 | 111 | Error | 5 ERROR |
| 8 | 1000 | Error | 5 ERROR |
| 9 | 1001 | Error | 5 ERROR |
| 10 | 1010 | Air above serum above gel above cells | 3 NORMAL |
| >11 | 1011 | Error | 6 ERROR |

Each condition corresponding to a transition code can be handled by a process that deals with the specific conditions leading to that code. This permits simpler and more reliable handling of the information. The output from these case handlers is a height for the top and bottom of the serum. If the amount of serum is insufficient or the possibility of the pipetting probe contacting the gel is too great, then the sampling process is aborted. If the pipetting probe contacts the gel or if there exists insufficient serum, an erroneous result is probable. On the other hand the pipetting probe can be moved to a position such that the opening is below the surface of the serum yet the outside of the pipetting probe is minimally exposed to serum so that carryover contamination is minimized. It is also possible to further level sense with the pipettor probe by means known in the art. The advantage is positioning the pipetting probe near the fluid interface decreases the distance that the probe needs to move while seeking a level. Often the seek speed is low compared to travel speed. Thus the speed of the sampling process is improved.

INCORPORATION OF REDUNDANT
Scan For Increased Reliability

An improved mode of operation is to scan the container from bottom to top as previously described and to further scan the container on returning the sensor element to its home position. The data processing has the task of reconciling the two scans and thereby improving the reliability of the process.

Table 2 illustrates the relations among the transition codes for the bottom to top (BT) and the top to bottom (TB) scans. A relation between the scans has been discovered, i.e., can be converted to the other by the process of reversing the order of the bits and complementing the result. To see this relation more clearly, consider BT code 110. On the return scan, the last capacitance is low, so there should be a transition to a high capacitance, corresponding to a start from a low capacitance represented by the rightmost of 0 of BT scan to the higher capacitance represented by the 1 to the left of the 0. Next is a transition to a low capacitance since the only way to achieve a 11 pattern (in 110) is to transition to a higher capacitance followed by a transition to an even higher capacitance. Finally there should be a low transition as the sensor element returns to the starting position which was low. Thus the bit pattern for the TB scan is 100.

The bit reversal considering only 3 bits of data is 001 and when complemented yields 110, which code is identical to the original code. The bit reversal process is well known in the Fast Fourier Transform, those conversion schemes could be used here. Alternatively, since the number of bits are small, a look-up table could be used. Thus, the code 100 can be interpreted as a value of eight. The eighth element in the table would contain the code 110.

Yet another way to achieve the comparable code from the TB scan is to fill the bits into the code word at bit position 1, then 2, then 3, etc. rather than shifting the current code left and filling in bit 1. Further, during the TB scan a zero could correspond to the low to high capacitance transition rather than the complement, i.e., one.

In all events, the process code for the BT scan should match the code from the TB scan, otherwise some error has occurred in scanning and the data are suspect.

TABLE 2

RELATION OF TRANSITION CODE FROM UP AND DOWN SCANS

| CON-DITION | BOTTOM TO TOP | TOP TO BOTTOM | TRAN-SITIONS in TB scan | TB SCAN bit reverse | REV AND BT |
|---|---|---|---|---|---|
| 0 | 0 | 1 | 0 | 1 | 0 |
| 1 | 1 | 0 | 1 | 0 | 0 |
| 2 | 10 | 10 | 2 | 01 | 00 |
| 3 | 11 | 00 | 2 | 00 | 00 |
| 4 | 100 | 110 | 3 | 011 | 000 |
| 5 | 101 | 010 | 3 | 010 | 000 |
| 6 | 110 | 100 | 3 | 001 | 000 |
| 7 | 111 | 000 | 3 | 000 | 000 |
| 8 | 1000 | 1110 | 4 | 0111 | 0000 |
| 9 | 1001 | 0110 | 4 | 0110 | 0000 |
| 10 | 1010 | 1010 | 4 | 0101 | 0000 |
| 11 | 1011 | 0010 | 4 | 0100 | 0000 |
| 12 | 1100 | 1100 | 4 | 0011 | 0000 |
| 13 | 1101 | 0100 | 4 | 0010 | 0000 |
| 14 | 1110 | 1000 | 4 | 0001 | 0000 |
| 15 | 1111 | 0000 | 4 | 0000 | 0000 |

FLOW CHART

The invention may be better understood with reference to FIGS. 3 to 6 in which flow charts are depicted which describe the software used by the CPU to control the acquisition of information relating to the interfaces and aliquoting the sample liquid.

FIG. 3: ACQUISITION OF NATURE AND POSITION OF INTERFACES

In process 110, the sensor element is commanded to start scanning up from below the bottom of the container. The status of the sensor is polled in decision point 120. If the probe element is at the top of travel, then control is passed to process 160 where the probe element is returned to the home position below the vessel. Otherwise the status of the sensor is polled, in decision point 130, for the occurrence of a transition. If there was no transition, control is passed back to decision point 120. Otherwise a transition has occurred and process 140 stores the nature (increase or decrease in capacitance) and height of the transition, and increments the count of number of transitions. Control is then passed back to decision point 120.

In process 160, the sensor element is commanded to return to home and start scanning from the current (top) position to below the bottom. Control is passed to decision point 170. If the probe element is at the bottom of travel, the scan is complete and the process is exited. Otherwise the status of the sensor is polled, in decision point 180, for the occurrence of a transition. If there was no transition, control is passed back to decision point 170. Otherwise a transition has occurred and process 190 stores the nature (increase or decrease in capacitance) and height of the transition, and increments the count of number of transitions. Control is then passed back to decision point 170.

FIG. 4: RECONCILIATION OF SCAN DATA

At decision point 310, the number of detected transitions is compared to an upper limit. If the number is outside of acceptable limits, the process is exited with a status of error. At decision point 320 the process compares the number of transitions in the top to bottom scan. If the number of transitions are not the same, then the process is exited with a status of error. Otherwise, at decision 340 the transition code word from the top to bottom scan is bit reversed. This may be accomplished by a simple look-up table or by processes developed for Fast Fourier Transform address reversal where the size of the address corresponds to the number of transitions here, and the address corresponds to the transition code here. The bottom to top scan is compared with the bit reversed, complimented, top to bottom scan. If the result is unequal, then the data are inconsistent and the process is exited with a status of error. Otherwise the process is exited with a status of good.

FIG. 5: RECOGNITION OF SAMPLE CONDITION

The value of the transition code is successively compared, in decision point 410, with the values 1 through 10 and greater than 10 and if true, control is passed to a process, numbered 421 through 426 corresponding to that condition (which process number is illustrated in Table X).

FIG. 6: ALIQUOTING OF SAMPLE FLUID

The pipettor probe is lowered in process 610 to a height that is computed such that only the tip of the pipettor probe is submerged into the serum so that the outside of the probe is minimally contaminated by the serum. When the pipettor probe has reached the computed height, control is passed to process 670 and the desired volume (aliquot) of fluid is withdrawn. Control is passed to process 680 where the pipettor probe is raised to the travel height following which process 690 moves the pipettor probe to a position where the serum is delivered to a reaction container and the determination of the desired constituents of the serum can take place.

Figure 2:
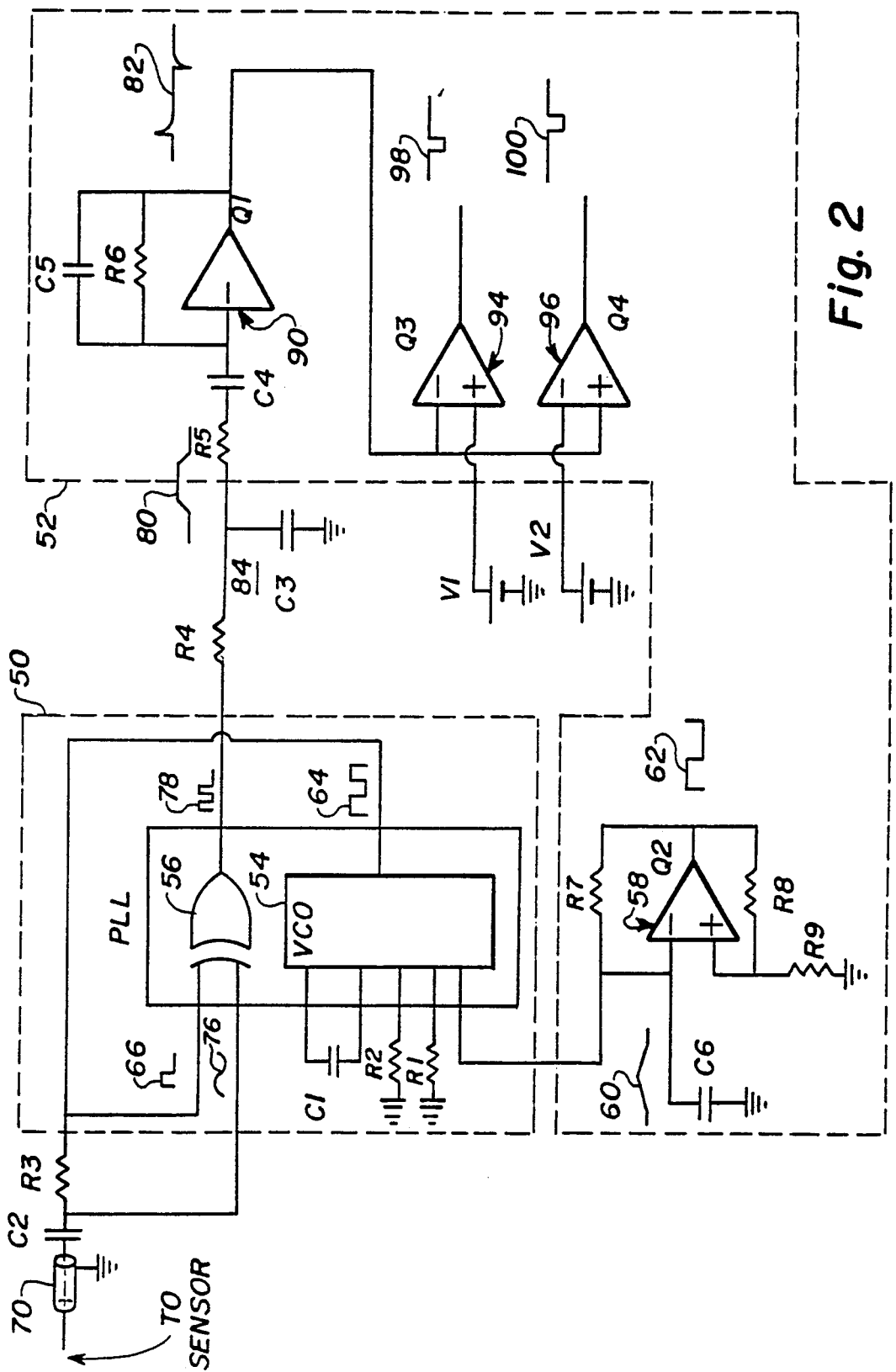
FIG. 2 is a schematic diagram of a preferred embodiment of the liquid interface sensor constructed in accordance with this invention.
Figure 3:
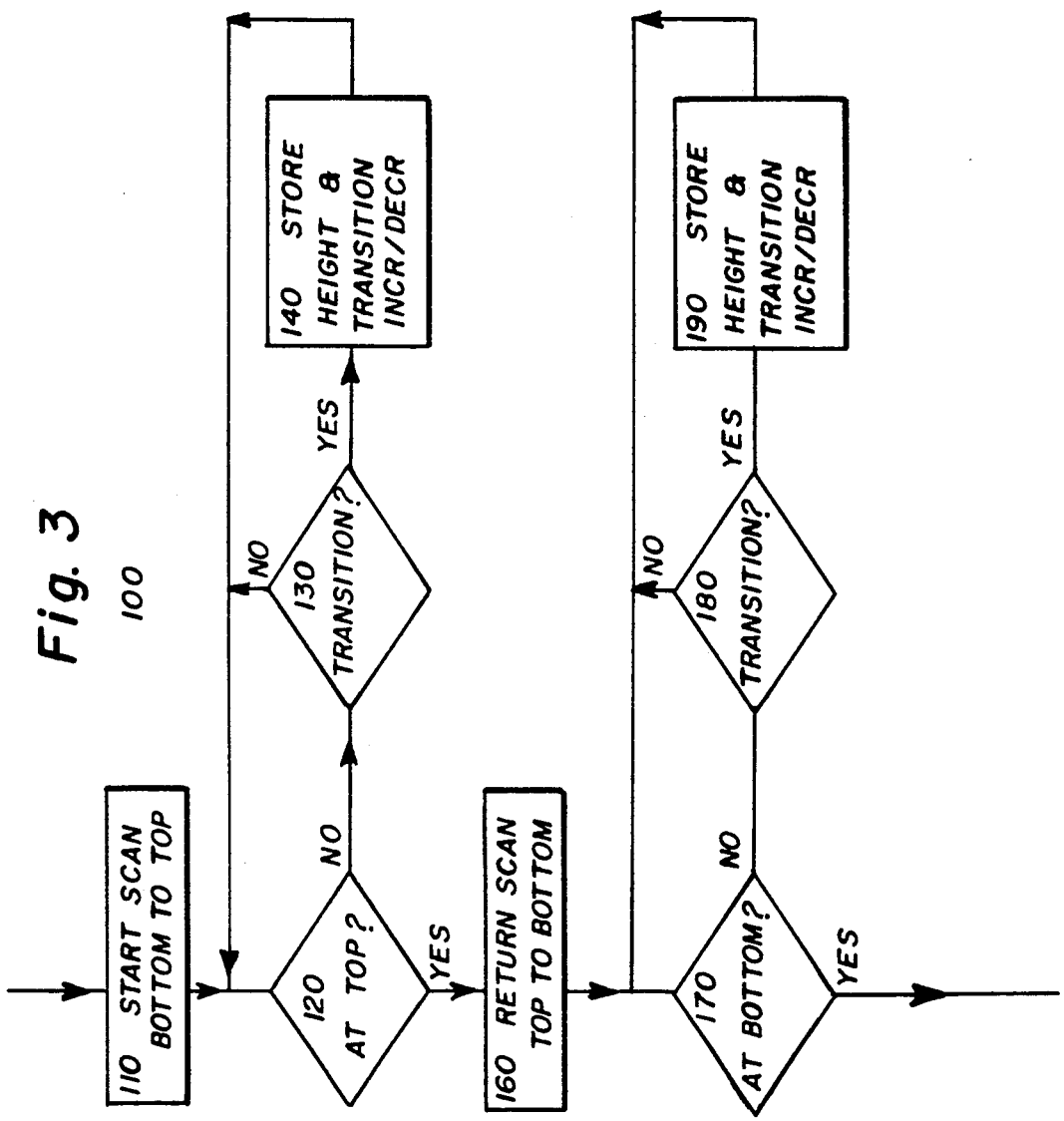
FIG. 3 is a flow chart depicting the manner in which the CPU controls the sensor of FIG. 1 to determine the nature and position of the liquid interfaces.

With reference to FIG. 2, a specific circuit constructed in accordance with the preferred embodiment of this invention for sensing layers is illustrated. In this circuit essentially two integrated circuit chips are used. The first is phase-locked loop which may use, for example, a CD4046BM chip made by National Semiconductor. In addition a quad operational amplifier chip made by Texas Instrument Company, TLC274CN may be used. The phase-lock loop is designated by the dashed block 50. Similarly, the quad operational amplifier is designated by the dashed block 52. The phase-lock loop includes a voltage control oscillator 54 and several phase comparators only one of which, 56, is shown. The voltage controlled oscillator 54 has several inputs which have been selected to provide a nominal 1 MHz by choice of resistors R1 and R2 and capacitor C1. The selection of these values is described in the application notes for the chip from National Semiconductor.

The VCO 54 is caused to sweep by a sweep oscillator in the form of an astable oscillator which is constructed as part of the quad operational amplifier chip 52. The sweep oscillator, designated 58, is constructed such that the output is applied through resistor R7 and capacitor C6 to the inverting input of the amplifier labelled Q2. Further, the output of Q2 is applied through resistors R8 and R9 to the noninverting input of the amplifier. Suppose that the output of the amplifier goes high. The voltage at the noninverting input will go high. The voltage at the inverting input will remain low because of capacitor C6. As charge accumulates on capacitor C6 a time will come when its voltage exceeds that of the noninverting input at which time the output of Q2 will swing low. In a similar fashion resistors R8 and R9 apply a low voltage to the noninverting input of Q2. Because of capacitor C6 the voltage at the inverting input will remain high.

This status will remain until the voltage across C6 is discharged to a voltage below that of the noninverting input at which time the output of Q2 will swing high and the cycle will repeat endlessly. In this circuit it is customary to take the voltage from the output which is a square wave 62. However to obtain a voltage sweep to provide a linear sweep of frequency of the oscillator, a sawtooth or triangular waveform is preferred. This is the signal found at the junction of R7 and C6. This approximately triangle wave 60 is applied to the VCO input. This signal causes the voltage controlled oscillator to sweep approximately 20 kHz around the nominal 1 MHz frequency. The rate at which it sweeps up and down is approximately 20 kHz and is determined by the values of the resistors R7, R8, and R9 and capacitor C6.

The output of the voltage controlled oscillator 54 is designated by the square waveform 64. The output of the VCO is applied to two portions. One portion is supplied to a phase comparator 56. This serves as the reference signal and is illustrated by the waveform 66. The other portion of the output of the VCO is supplied to an RC phase shifter composed of elements R3, C2 and the sensing element. Capacitor C2 is used as the D.C. blocking capacitor. The actual capacitance affecting the phase shift is composed of the capacitance of the coaxial cable labelled 70 and the capacitances to ground of the sensing element 10. The element is metal as described. The junction between R3 and C2 is a signal labelled 76 and the signal from the element that is affected by the dielectric of the sample. This signal 76 is an RC smoothed triangle wave and is applied to the signal input of phase comparator 56.

Phase comparator 56 is of the exclusive OR variety. The output of the phase comparator is a series of pulses, the width of which depends on the phase difference between the reference signal 66 and the input signal 76.

The output of the phase comparator 56, in the form of the square wave 78, is applied to an RC filter network 84 composed of resistor R4 and C3. The purpose of this filter is to remove the pulses from the phase comparator and produce an approximate D.C. level proportionate to the area of the waveform 78. If the pulse width of 78 changes then the approximately D.C. level of the filter 84 will change. The changing D.C. level is represented by the waveform 80 which is applied to a differentiator 90, the heart of which is an operational amplifier Q1, a member of the quad operational amplifier 52. Thus, to effect the differentiation, the output of the RC filter 84 is applied through resistor R5 and capacitor C4 to the input of the amplifier 90. The feedback portion of the amplifier 90 is composed of R6 and C5 in parallel. These components have been selected to form a differentiator for low frequencies, namely the changing portion of waveform 80. These components also filter out high frequency noise that might leak through the filter network 84.

The output of the differentiator 90 is in the form of pulses, the height of which is dependent on the rate of change and extent of change of waveform 80. This output signal is represented by the waveform 82. These pulses can then be discriminated with a window comparator to select pulses of sufficient amplitude to represent a useful transition in the capacitances at the probe which, of course, is sensitive to the dielectric effect of the sample. The window comparator is composed of amplifiers of operational amplifiers 52 labelled 94 and 96. In these amplifiers the signal level is compared against the voltage labelled V1 and V2. For example, if the input voltage to 94 is applied to the inverting input whenever the input voltage is below V1 the output will be high. For the period of time that the input voltage rises above V1 the output will remain low. Thus, the positive going pulse in waveform 82 causes a negative going pulse in waveform 98.

In a similar fashion the negative going pulse in waveform 82 appears as a negative going pulse from circuit 96 and has a waveform labelled 100. The two waveforms 98 and 100 are the outputs of the circuit. Waveform 98 has a negative going pulse whenever the element encounters an increase in capacitance as when it is proximate a high dielectric material. Waveform 98 has a negative going element whenever the probe encounters a liquid interface of increasing conductance or dielectric constant. In a similar fashion, waveform 100 is a negative going pulse whenever the element decreases in capacitance, i.e., when it encounters an interface of decreasing conductance or dielectric constant.

The method of this invention detects liquid interfaces which occur in any container with different layers, preferably of immiscible liquids, in order to determine if the container can be sampled properly without contacting unwanted layers. It offers a redundancy that verifies the accuracy of the detection and thus enhances the accuracy of the sample.

What is claimed is:

1. A method for controlling the sampling of liquids from a container by a prove, the liquids being held in a container having a generally vertical axis, comprising the steps of:
   scanning along the container axis in a first sense to detect increasing or decreasing capacitance transitions therein,
   cumulating each such transition,
   recording the height along the axis corresponding to each said transition,
   actuating the probe to sample the container only if the proper number of transitions has occurred, and
   controlling the depth at which the probe samples in accordance with the said recorded heights.

2. A method according to claim 1 which includes disabling the probe when the cumulated transitions do not equal a predetermined number.

3. A method for controlling the sampling of liquids from a container having a generally vertical axis, comprising the steps of:
   scanning along the container axis in a first sense to detect the increasing or decreasing capacitance transitions therein,
   forming a first bindary code by, at each such transition, shifting the bits of the first binary code to the left one bit and adding "1" to the rightmost position if the transition is of increasing nature,
   recording the height along said axis corresponding to said transition,
   actuating the probe to sample the container only if the first binary code matches a predetermined value, and
   controlling the depth at which the probe samples liquid in accordance with the said recorded heights.

4. The method of claim 3 which includes the additional steps of:
   (a) scanning along the container axis in a second sense opposite the first sense to detect increasing or decreasing capacitance transitions therein,
   (b) forming a second binary code, at each such transition, shifting the bits of the second binary code the left one bit and adding "1" to the rightmost position if the transition is of increasing nature, and 5. The method of claim 4 wherein the codes are reconciled by the steps of:
   (d) reversing the order of the bits of the secondary binary code,
   (e) complementing the result of step and
   (f) comparing the result of step (e) with the first binary code for equality.

6. The method of claim 4 wherein the codes are reconciled by the steps of:
   (a) providing a lookup table that provides a corresponding code for the second code, and
   (b) comparing the second and the corresponding codes for equality.

* * * * *